United States Patent [19]

Kameswaran et al.

[11] Patent Number: 5,157,047

[45] Date of Patent: Oct. 20, 1992

[54] BIS- AND TRIS(TRIFLUOROMETHYL)ARYLPYRROLE INSECTICIDAL AND ACARICIDAL AGENTS

[75] Inventors: Venkataraman Kameswaran, Princeton Junction; Victor M. Kamhi, Hamilton Sq., both of N.J.

[73] Assignee: American Cyanamid Company, Stamford, Conn.

[21] Appl. No.: 600,054

[22] Filed: Oct. 18, 1990

[51] Int. Cl.$^5$ .................... A01N 43/36; C07D 207/30
[52] U.S. Cl. ..................................... 514/423; 514/427; 548/530; 548/539; 548/540; 548/560; 548/561
[58] Field of Search ............... 548/560, 561, 539, 540, 548/530; 514/423, 427

[56] References Cited

U.S. PATENT DOCUMENTS 3,428,648  2/1969  Umio ................................... 548/560

OTHER PUBLICATIONS

Ser. No. 07/392,495, filed Aug. 11, 1989.

*Primary Examiner*—Mary C. Lee
*Assistant Examiner*—Joseph K. McKane
*Attorney, Agent, or Firm*—John W. Hogan, Jr.

[57] ABSTRACT

Bis- and tris(trifluoromethyl)arylpyrrole compounds which are effective for the control of insects and acarids are described. A method for the insecticidal and acaricidal use of said compounds and methods for the preparation of said compounds are presented.

14 Claims, No Drawings

BIS- AND TRIS(TRIFLUOROMETHYL)ARYLPYRROLE INSECTICIDAL AND ACARICIDAL AGENTS

SUMMARY OF THE INVENTION

The present invention describes bis- and tris(trifluoromethyl)arylpyrrole compounds that are highly effective insecticidal and caracidal agents useful for the control of insect and acarid pests and for protecting agronomic crops from the ravages of said pests.

The bis- and tris(trifluoromethyl)arylpyrrole compounds of the present invention have the structural formula I

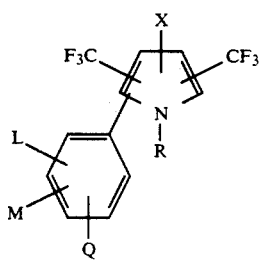

wherein
L is H, Cl, Br or F;
M and Q are each independently H, F, Cl, Br, CN, $NO_2$, $CF_3$, $C_1-C_4$ alkyl or $C_1-C_3$ alkoxy;
X is Cl, Br, I or $CF_3$; R is

hydrogen, cyano, $C_1-C_6$ alkyl optionally substituted with one to three halogen atoms,
one tri($C_1-C_4$ alkyl)silyl,
one hydroxy,
one cyano,
one or two $C_1-C_4$ alkoxy groups optionally substituted with one to three halogen atoms,
one $C_1-C_4$ alkylthio,
one phenyl optionally substituted with one to three halogen atoms, one to three $C_1-C_4$ alkyl groups or one to three $C_1-C_4$ alkoxy groups,
one phenoxy group optionally substituted with one to three halogen atoms, one to three $C_1-C_4$ alkyl groups or one to three $C_1-C_4$ alkoxy groups,
one benzyloxy group optionally substituted on the phenyl ring with one to three halogen atoms, one to three $C_1-C_4$ alkyl groups or one to three $C_1-C_4$ alkoxy groups,
one $C_1-C_6$ alkylcarbonyloxy group optionally substituted with one to three halogen atoms,
$C_2-C_6$ alkenylcarbonyloxy group optionally substituted with one to three halogen atoms,
one phenylcarbonyloxy group optionally substituted with one to three halogen atoms, one to three $C_1-C_4$ alkyl groups or one to three $C_1-C_4$ alkoxy groups,
one $C_1-C_6$ alkoxycarbonyl group optionally substituted with one to three halogen atoms or one to three $C_1-C_4$ alkoxy groups, or
one benzyloxycarbonyl group optionally substituted on the phenyl ring with one to three halogen atoms, one to three $C_1-C_4$ alkyl groups or one to three $C_1-C_4$ alkoxy groups,
$C_3-C_6$ alkenyl optionally substituted with one to three halogen atoms or one phenyl group, or
$C_3-C_6$ alkynyl optionally substituted with one to three halogen atoms or one phenyl group; and
$R_1$ is $C_1-C_6$ alkyl optionally substituted with one to three halogen atoms,
one hydroxy,
one cyano,
one or two $C_1-C_4$ alkoxy groups optionally substituted with one to three halogen atoms,
one $C_1-C_4$ alkylthio,
one phenyl optionally substituted with one to three halogen atoms, one to three $C_1-C_4$ alkyl groups or one to three $C_1-C_4$ alkoxy groups,
one phenoxy group optionally substituted with one to three halogen atoms, one to three $C_1-C_4$ alkyl groups or one to three $C_1-C_4$ alkoxy groups,
one benzyloxy group optionally substituted on the phenyl ring with one to three halogen atoms, one to three $C_1-C_4$ alkyl groups or one to three $C_1-C_4$ alkoxy groups,
one $C_1-C_6$ alkylcarbonyloxy group optionally substituted with one to three halogen atoms,
one $C_2-C_6$ alkenylcarbonyloxy group optionally substituted with one to three halogen atoms,
one phenylcarbonyloxy group optionally substituted with one to three halogen atoms, one to three $C_1-C_4$ alkyl groups or one to three $C_1-C_4$ alkoxy groups,
one $C_1-C_6$ alkoxycarbonyl group optionally substituted with one to three halogen atoms or one to three $C_1-C_4$ alkoxy groups, or
one benzyloxycarbonyl group optionally substituted on the phenyl ring with one to three halogen atoms, one to three $C_1-C_4$ alkyl groups or one to three $C_1-C_4$ alkoxy groups,
$C_3-C_6$ alkenyl optionally substituted with one to three halogen atoms or one phenyl group,
$C_3-C_6$ alkynyl optionally substituted with one to three halogen atoms or one phenyl group,
phenyl optionally substituted with one to three halogen atoms, one or two $C_1-C_4$ alkyl groups, one or two $C_1-C_4$ alkoxy groups, $CF_3$, CN, $NO_2$, di($C_1-C_4$ alkyl)amino or $C_1-C_4$ alkanoylamino,
phenoxy optionally substituted with one to three halogen atoms, one or two $C_1-C_4$ alkyl groups, one or two $C_1-C_4$ alkoxy groups, $CF_3$, CN, $NO_2$, di($C_1-C_4$ alkyl)amino or $C_1-C_4$ alkanoylamino,
$C_1-C_6$ alkoxy optionally substituted with one to three halogen atoms,
$C_2-C_6$ alkenyloxy optionally substituted with one to three halogen atoms,
di($C_1-C_4$ alkyl)amino,
N-($C_1-C_4$alkyl)-N-phenylamino or -N-halophenylamino, or
$C_3-C_6$ polymethyleneimino; provided that when the pyrrole ring is substituted with $CF_3$ at each of the pyrrole carbon atoms adjacent to the ring nitrogen atom and X is Cl, Br or I then R cannot be hydrogen.

DETAILED DESCRIPTION OF THE INVENTION

The compounds of the present invention are excellent insecticidal and acaricidal agents. The present invention provides a method for controlling undesirable pests by applying a pesticidally effective amount of a bis- or tris(trifluoromethyl)arylpyrrole compound to the breeding grounds, food supply or habitat of said pests. Preferred groups of bis- and tris(trifluoromethyl)arylpyrroles are illustrated by formula II and formula III

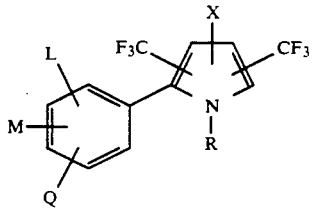

(II)

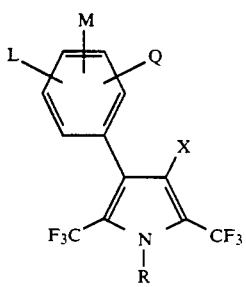

(III)

wherein L, M, Q, X R and $R_1$, are as described above; provided that in Formula III when X is Cl, Br or I then R cannot be hydrogen Preferred formula I bis- and tris(trifluoromethyl)-arylpyrroles of the invention are those in
X is Br or $CF_3$;
L is H;
M is H, F, Cl or Br;
Q is H, F, Cl, Br or $CF_3$;
R is

hydrogen, cyano,
$C_1$-$C_6$ alkyl optionally substituted with one to three halogen atoms,
one tri($C_1$-$C_4$ alkyl)silyl,
one cyano,
one or two $C_1$-$C_4$ alkoxy groups,
one phenoxy group,
one benzyloxy group,
one $C_1$-$C_6$ alkylcarbonyloxy group,
one $C_2$-$C_6$ alkenylcarbonyloxy group,
one phenylcarbonyloxy group,
one $C_1$-$C_6$ alkoxycarbonyl group, or
one benzyloxycarbonyl group,
$C_3$-$C_6$ alkenyl, or
$C_3$-$C_6$ alkynyl; and $R_1$ is $C_1$-$C_6$ alkyl optionally substituted with one to three halogen atoms, one cyano, one or two $C_1$-$C_4$ alkoxy groups, one phenyl, one phenoxy group, one benzyloxy group, one $C_1$-$C_6$ alkylcarbonyloxy group, one $C_2$-$C_6$ alkenylcarbonyloxy group, one phenylcarbonyloxy group, one $C_1$-$C_6$ alkoxycarbonyl group, or one benzyloxycarbonyl group, $C_3$-$C_6$ alkenyl, $C_3$-$C_6$ alkynyl, phenyl, phenoxy, $C_1$-$C_6$ alkoxy, $C_2$-$C_6$ alkenyloxy; provided that when the pyrrole ring is substituted with $CF_3$ at each of the pyrrole carbon atoms adjacent to the ring nitrogen atom and X is Br then R cannot be hydrogen.

Preferred formula II compounds which are especially effective as insecticidal and/or acaricidal agents are those in which
L is H, Cl, Br or F;
M and Q are each independently H, F, Cl, Br, CN, $NO_2$ or $CF_3$;
X is Cl, Br, I or $CF_3$;
R is

hydrogen, cyano or $C_1$-$C_6$ alkyl optionally substituted with one to three halogen atoms, CN, $C_1$-$C_4$ alkoxy, $C_1$-$C_6$ alkylcarbonyloxy or benzyloxycarbonyl; and $R_1$ is phenyl optionally substituted with one to three halogen atoms.

Bis(trifluoromethyl)arylpyrrole compounds of formula II may be prepared by reacting an acetophenone oxime or a substituted acetophenone oxime represented by the structural formula IV

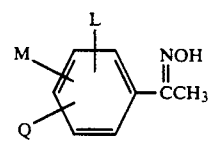

(IV)

wherein L is H, Cl, Br or F; M and Q are each independently H, F, $C_1$, Br, CN, $No_2$, $CF_3$, $C_1$-$C_4$ alkyl or $C_1$-$C_3$ alkoxy; with at least an equivalent amount of commercially available hexafluoro-2-butyne and a base such as an alkali metal alkoxide in the presence of a solvent to give both the appropriately substituted O-[1,2-bis(trifluoromethyl)vinyl]-acetophenone oxime, vinyl-(Z) represented by formula V and the appropriately substituted 2-aryl-4,5-trans-bis-(trifluoromethyl)-1-pyrrolin-5-ol represented by formula VI. The O-[1,2-bis(trifluoromethyl)vinyl]-acetophenone oxime, vinyl-(Z) is then heated in the presence of a solvent at an elevated temperature range (e.g. 80° to 190° C.) to form 2-aryl-4,5-bis(trifluoromethyl)-1-pyrrolin-4-ol, trans- and cis-represented by structural formula VII. The 2-aryl-4,5-trans-bis(trifluoromethyl)-1-pyrrolin-5-ol or 2-aryl-4,5-bis(trifluoromethyl)-1-pyrrolin-4-ol, trans- or cis- compounds are then reacted with at least an equivalent amount of hydrochloric acid in an alcohol to obtain a 5-aryl-2,3-bis(trifluoromethyl)pyrrole. The 5-aryl-2,3-bis(trifluoromethyl)pyrrole is then reacted with at least an equivalent amount of a halogenating agent in the presence of a solvent to obtain the formula II bis(trifluoromethyl)arylpyrrole wherein L, M and Q are as described above and X is Cl, Br or I. Halogenating agents that may be employed include sodium hypochlorite, bromine, N-bromosuccinimide, chlorine, N-chlorosuccinimide, sulfuryl chloride, sulfuryl bromide, tert-butylhypochlorite, iodine, N-iodosuccinimide and the like. Solvents suitable for use in the above reaction include dioxane, tetrahydrofuran, acetic acid or a chlorinated hydrocarbon solvent. The reactions are illustrated in Flow Diagram I.

FLOW DIAGRAM I

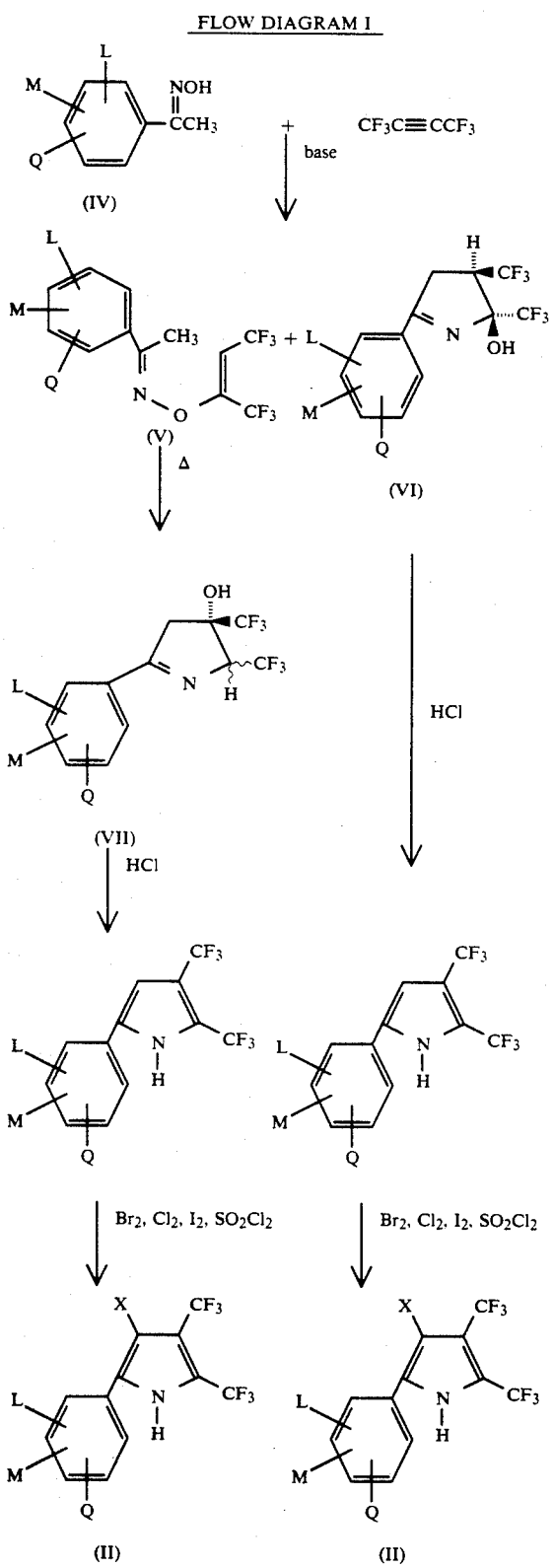

Similarly, other formula II bis(trifluoromethyl)aryl-pyrroles may be prepared by the halogenation of 2-aryl-3,5-bis(trifluoromethyl)pyrroles, which are described in copending U.S. patent application Ser. No.392,495, filed on Aug. 11, 1989 and which is incorporated herein by reference thereto, by using the above-mentioned halogenating techniques as illustrated below

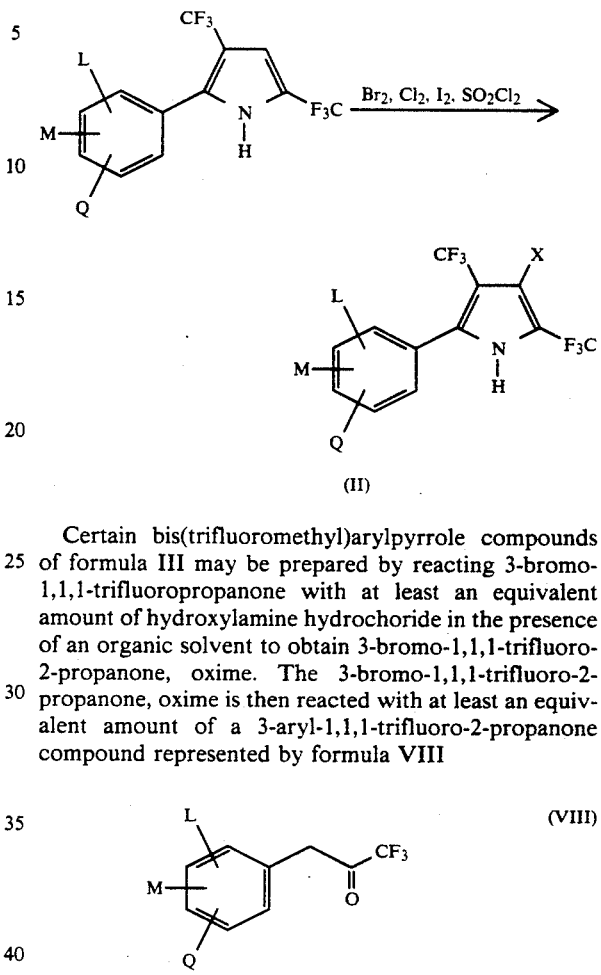

Certain bis(trifluoromethyl)arylpyrrole compounds of formula III may be prepared by reacting 3-bromo-1,1,1-trifluoropropanone with at least an equivalent amount of hydroxylamine hydrochoride in the presence of an organic solvent to obtain 3-bromo-1,1,1-trifluoro-2-propanone, oxime. The 3-bromo-1,1,1-trifluoro-2-propanone, oxime is then reacted with at least an equivalent amount of a 3-aryl-1,1,1-trifluoro-2-propanone compound represented by formula VIII

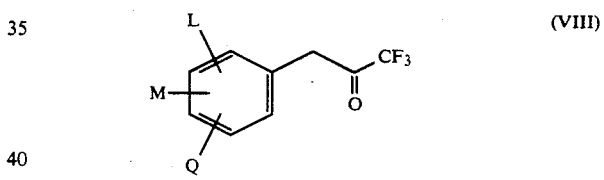

wherein

L is H, Cl, Br or F;

M and Q are independently H, F, Cl, Br, CN, $NO_2$, $CF_3$, $C_1$-$C_4$ alkyl or $C_1$-$C_3$ alkoxy; in the presence of at least an equivalent amount of a base such as an alkali metal alkoxide in an organic solvent to give the appropriately substituted 3-aryl-1,1,1,6,6,6-hexafluoro-2,5-hexanedione, 5-oxime. The 3-aryl-1,1,-1,6,6,6-hexafluoro-2,5-hexanedione, 5-oxime is then reacted with at least an equivalent amount of hydrochloric acid in an alcohol to obtain a 3-aryl-2,5-bis(trifluoromethyl)-1-hydroxypyrrole. The said hydroxypyrrole intermediate is then reacted with at least an equivalent amount of zinc in a solvent such as acetic acid to give 3-aryl-2,5-bis(trifluoromethyl)pyrrole. The resultant 3-aryl-2,5-bis(trifluoromethyl)pyrrole is then reacted with at least one molar equivalent of a halogenating agent in the presence of a solvent to give a bis(trifluoromethyl)aryl-pyrrole compound represented by formula IX wherein L, M, and Q are as described above and X is Cl, Br or I. The formula IX bis(trifluoromethyl)arylpyrrole is then reacted with an alkylating, acylating or cyanating agent such as, cyanogen bromide, p-chlorobenzoyl chloride, methyl iodide, chloromethyl ethyl ether and the like in the presence of a base such as an alkali metal alkoxide in an organic solvent to obtain the formula III bis(trifluoromethyl)arylpyrrole wherein L, M, Q and X are as described above and
R is

cyano
$C_1-C_6$ alkyl optionally substituted with one to three halogen atoms,
one tri($C_1-C_4$ alkyl)silyl,
one hydroxy,
one cyano,
one or two $C_1-C_4$ alkoxy groups optionally substituted with one to three halogen atoms,
one $C_1-C_4$ alkylthio,
one phenyl optionally substituted with one to three halogen atoms, one to three $C_1-C_4$ alkyl groups or one to three $C_1-C_4$ alkoxy groups,
one phenoxy group optionally substituted with one to three halogen atoms, one to three $C_1-C_4$ alkyl groups or one to three $C_1-C_4$ alkoxy groups,
one benzyloxy group optionally substituted on the phenyl ring with one to three halogen atoms, one to three $C_1-C_4$ alkyl groups or one to three $C_1-C_4$ alkoxy groups,
one $C_1-C_6$ alkylcarbonyloxy group optionally substituted with one to three halogen atoms,
one $C_2-C_6$ alkenylcarbonyloxy group optionally substituted with one to three halogen atoms,
one phenylcarbonyloxy group optionally substituted with one to three halogen atoms, one to three $C_1-C_4$ alkyl group or one to three $C_1-C_4$ alkoxy groups,
one $C_1-C_6$ alkoxycarbonyl group optionally substituted with one to three halogen atoms or one to three $C_1-C_4$ alkoxy groups, or
one benzyloxycarbonyl group optionally substituted on the phenyl ring with one to three halogen atoms, one to three $C_1-C_4$ alkyl groups or one to three $C_1-C_4$ alkoxy groups,
$C_3-C_6$ alkenyl optionally substituted with one to three halogen atoms or one phenyl group, or
$C_3-C_6$ alkynyl optionally substituted with one to three halogen atoms or one phenyl group; and
$R_1$ is $C_1-C_6$ alkyl optionally substituted with one to three halogen atoms,
one hydroxy,
one cyano,
one or two $C_1-C_4$ alkoxy groups optionally substituted with one to three halogen atoms,
one $C_1-C_4$ alkylthio,
one phenyl optionally substituted with one to three halogen atoms, one to three $C_1-C_4$ alkyl groups or one to three $C_1-C_4$ alkoxy groups,
one phenoxy group optionally substituted with one to three halogen atoms, one to three $C_1-C_4$ alkyl groups or one to three $C_1-C_4$ alkoxy groups,
one benzyloxy group optionally substituted on the phenyl ring with one to three halogen atoms, one to three $C_1-C_4$ alkyl groups or one to three $C_1-C_4$ alkoxy groups,
one $C_1-C_6$ alkylcarbonyloxy group optionally substituted with one to three halogen atoms,
one $C_2-C_6$ alkenylcarbonyloxy group optionally substituted with one to three halogen atoms,
one phenylcarbonyloxy group optionally substituted with one to three halogen atoms, one to three $C_1-C_4$ alkyl groups or one to three $C_1-C_4$ alkoxy groups,
$C_1-C_6$ alkoxycarbonyl group optionally substituted with one to three halogen atoms or one to three $C_1-C_4$ alkoxy groups, or
one benzyloxycarbonyl group optionally substituted on the phenyl ring with one to three halogen atoms, one to three $C_1-C_4$ alkyl groups or one to three $C_1-C_4$ alkoxy groups,
$C_3-C_6$ alkenyl optionally substituted with one to three halogen atoms or one phenyl group,
$C_3-C_6$ alkynyl optionally substituted with one to three halogen atoms or one phenyl group,
phenyl optionally substituted with one to three halogen atoms, one or two $C_1-C_4$ alkyl groups, one or two $C_1-C_4$ alkoxy groups, $CF_3$, CN, $NO_2$, di($C_1-C_4$ alkyl)amino or $C_1-C_4$ alkanoylamino,
phenoxy optionally substituted with one to three halogen atoms, one or two $C_1-C_4$ alkyl groups, one or two $C_1-C_4$ alkoxy groups, $CF_3$, CN, $NO_2$, di($C_1-C_4$ alkyl)amino or $C_1-C_4$ alkanoylamino,
$C_1-C_6$ alkoxy optionally substituted with one to three halogen atoms,
$C_2-C_6$ alkenyloxy optionally substituted with one to three halogen atoms,
di($C_1-C_4$ alkyl)amino,
N-($C_1-C_4$ alkyl)-N-phenylamino or -N-halophenylamino, or
$C_3-C_6$ polymethyleneimino.

The above reaction scheme is illustrated in Flow Diagram II.

FLOW DIAGRAM II

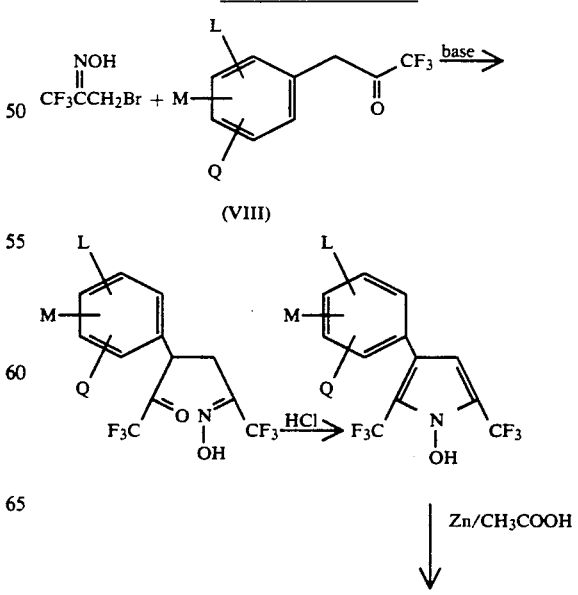

-continued
FLOW DIAGRAM II

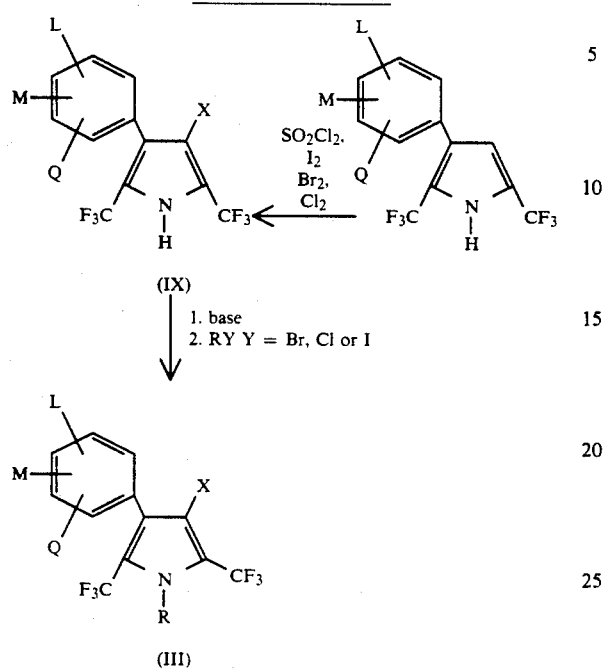

The formula I tris(trifluoromethyl)arylpyrrole compounds of the present invention may be prepared by reacting the formula VIII 3-aryl-1,1,1-trifluoro-2-propanone with at least one molar equivalent of hydroxylamine hydrochloride in a solvent to give 3-aryl-1,1,1-trifluoro-2-propanone, oxime. The resulting oxime is then reacted in a pressure bottle with at least an equivalent amount of liquid hexafluoro-2-butyne in the presence of at least a ten mole percent amount of a base such as an alkali metal alkoxide in a solvent at an elevated temperature range (e.g. 50°-80° C.) to obtain 3-aryl-5a-hydroxy-2,4-a, 5 b-tris(trifluoromethyl)-1-pyrroline. The said pyrroline is then reacted with at least one molar equivalent of hydrochloric acid in an alcohol to give the formula I tris(trifluoromethyl)arylpyrrole compounds as illustrated below in Flow Diagram III.

FLOW DIAGRAM III

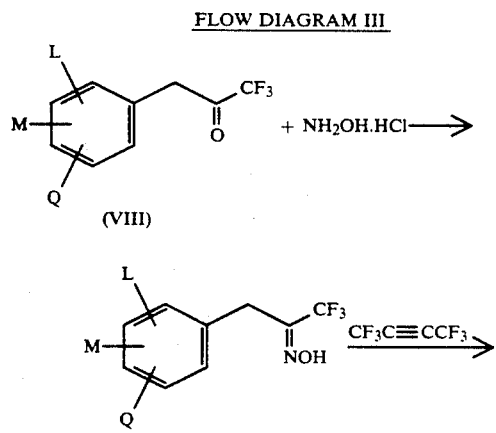

-continued
FLOW DIAGRAM III

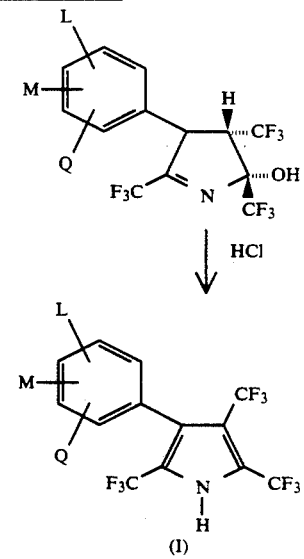

Formula II compounds of the present invention may be prepared by reacting a methyl N[(trimethylsilyl)methyl]thio benzimidate with at least a molar equivalent of commercially available 2,3-dichlorohexafluorobutene in a solvent to obtain 2-aryl-3,4-bis (trifluoromethyl)-pyrrole. The resultant bis(trifluoromethyl)pyrrole is halogenated by conventional techniques to give formula II bis(trifluoromethyl)arylpyrroles. The above reactions are illustrated in Flow Diagram IV.

FLOW DIAGRAM IV

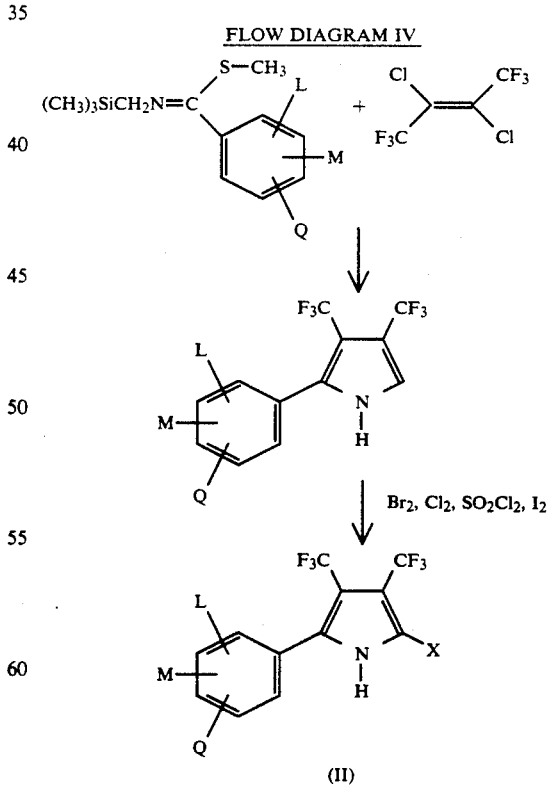

Preparation of R-substituted formula I bis- and tris(-trifluoromethyl)arylpyrrole compounds can be achieved by reaction of the appropriately substituted formula I bis- or tris(trifluoromethyl)arylpyrrole having R as hydrogen with an alkylating or acylating agent in the presence of an alkali metal alkoxide or hydride. For example, a formula I bis- or tris(trifluoromethyl)arylpyrrole, wherein R is hydrogen and X, L, M, and Q are as described for formula I above, is reacted with an appropriate alkylating agent such as a $C_1$–$C_6$ alkylhalide in which the alkyl group is straight or branched and is optionally substituted with from one to three halogen atoms, one hydroxy, one cyano, one $C_1$–$C_4$ alkoxy, one $C_1$–$C_4$ alkylthio, one phenyl group, optionally substituted with from one to three halogen atoms, or one benzyloxy group, optionally substituted with from one to three halogen atoms, and an alkali metal alkoxide such as sodium or potassium t-butoxide. This reaction provides a bis- or tris(trifluoromethyl)arylpyrrole having the same substitutents as the starting material, but in addition is substituted on the nitrogen with a $C_1$–$C_6$ alkyl group optionally substituted as described above. This reaction may be illustrated as follows:

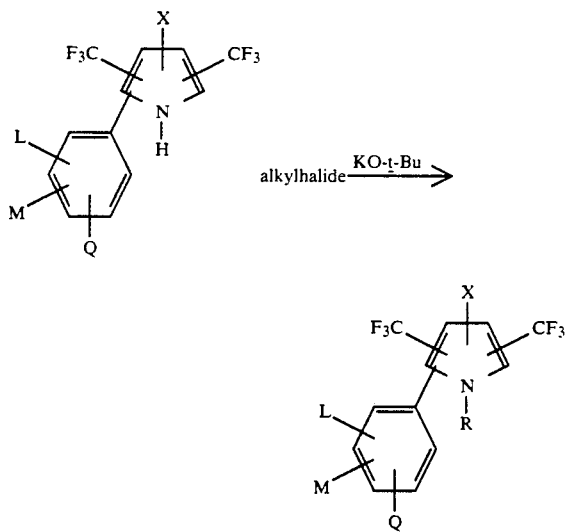

In a similar reaction cyanogen bromide is substituted for the alkylhalide and yields the formula I bis- or tris(trifluoromethyl)arylpyrrole having a carbonitrile, rather than an alkyl group, on the nitrogen.

Advantageously, the above-described alkylation procedure of the formula I bis- or tris(trifluoromethyl)arylpyrrole compounds, in which R is hydrogen, may also be applied to the preparation of formula I bis- or tris(trifluoromethyl)arylpyrroles having an N-$C_3$–$C_6$ alkenyl or N-$C_3$–$C_6$ alkynyl substituent. This N-substitution is obtained by simply substituting a $C_3$–$C_6$ alkenyl halide or $C_3$–$C_6$ alkynyl halide for the $C_1$–$C_6$ alkyl halide in the above-described reaction.

In a similar manner, preparation of N-acylated bis- or tris(trifluoromethyl)arylpyrrole compounds may be achieved by the reaction of an appropriately substituted formula I bis- or tris(trifluoromethyl)arylpyrrole wherein R is hydrogen with an acylating agent in the presence of an alkali metal alkoxide. Acylating agents such as $C_1$–$C_6$ alkyl or $C_2$–$C_6$ alkenyl acid chloride, substituted $C_1$–$C_6$ alkyl or $C_2$–$C_6$ alkenyl acid chloride, benzoyl chloride, substituted benzoyl chloride, phenylchloroformate, substituted phenylchloroformate, $C_1$–$C_6$ alkyl or $C_2$–$C_6$ alkenylchloroformate, substituted $C_1$–$C_6$ alkyl or $C_2$–$C_6$ alkenylchloroformate, N-substituted carbamoyl chloride and the like may be employed. The reaction may be illustrated as follows:

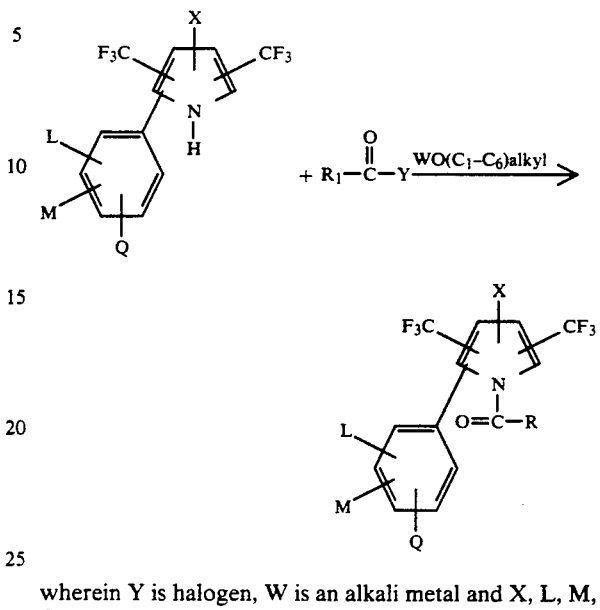

wherein Y is halogen, W is an alkali metal and X, L, M, Q and $R_1$ are as described hereinabove for formula I.

The bis- and tris(trifluoromethyl)arylpyrroles pyrroles of the present invention are effective for controlling insects and acarina. These compounds are also effective for protecting growing or harvested crops from attack by the above-said pests.

In practice generally about 10 ppm to 10,000 ppm and preferably 100 ppm to about 5,000 ppm of a formula I bis- or tris(trifluoromethyl)arylpyrrole, dispersed in water, or another inexpensive liquid carrier, is effective when applied to the plants, the crops or the soil in which said crops are growing to protect said crops from attack by insects and/or acarina.

The formula I bis- and tris(trifluoromethyl)arylpyrroles of this invention are also effective for controlling insects and acarina when applied to the foliage of plants and/or to the soil or water in which said plants are growing in sufficient amount to provide a rate of from about 0.1 Kg/ha to 4.0 Kg/ha of active ingredient.

While the bis- and tris(trifluoromethyl)arylpyrroles of this invention are effective for controlling insects and acarina when employed alone, they may also be used in combination with other biological chemicals, including other insecticides and acaricides. For example, the bis- and tris(trifluoromethyl)arylpyrroles of this invention may be used effectively in conjunction or combination with phosphates, carbamates, pyrethroids, formamidines, chlorinated hydrocarbons, halobenzoylureas and the like.

Advantageously, the above-said bis- and tris(trifluoromethyl)arylpyrroles may be formulated into dry compacted granules, suspension concentrates, wettable powders, dusts concentrates, emulsifiable concentrates, granular formulations, flowable compositions, microemulsions and the like, all of which lend themselves to soil, water and/or foliage application and provide the requisite plant protection. Such formulations include the compounds of the invention admixed with inert, pharmacologically-acceptable solid or liquid diluents.

A typical suspension concentrate formulation may be prepared by grinding together about 5% to 25% by weight of a formula I bis- or tris(trifluoromethyl)aryl-pyrrole, about 3% to 20% by weight of an anoinic surfactant such as dodecyl benzene sulfonic acid, about 1% to 5% by weight of a nonionic surfactant such as an ethylene oxide block copolymer having about 8 to 11 mols of ethoxylation, about 1% to 5% by weight of an alkylphenol polyethylene oxide condensate with 9 to 10 mols of ethoxylation and q.s. to 100% with a petroleum aromatic solvent.

Wetable powders, dusts and dust concentrate formulations of the invention can be prepared by grinding together about 3% to 20%, by weight, of the formula I bis- or tris(trifluoromethyl)arylpyrrole compound, with about 3% to 20% by weight of a solid anionic surfactant. One suitable anionic surfactant is a dioctyl ester of sodium sulfosuccinic acid, specifically Aerosol OTB ® surfactant, marketed by the American Cyamamid Company. About 60% o 94%, by weight, of an inert solid diluent, such as montmorillonite, attapulgite, chalk, talc, kaolin, diatomaceous earth, limestone, silicates or the like also is used in such formulations.

Compacted granules especially useful for soil or water application can be prepared by grinding together in about equal parts, usually about 3 to 20 parts of the bis- or tris(trifluoromethyl)arylpyrrole and a solid surfactant, with about 60 to 94 parts of gypsum. Thereafter, the mixture is compacted into small granular particles, about 24/48 mesh or larger.

Other suitable solid surfactants useful in the present formulations include not only the anionic dioctyl ester of sodium sulfosuccinic acid but also nonionic block copolymers of ethylene oxide and propylene oxide. Such block copolymers are marketed by BASF Wyandotte Corporation as Pluronic 10R8,, 17R8, 25R8, F28, F68, F77, or F87, and are especially effective for the preparation of compacted granules.

In addition to the powders and concentrate formulations described hereinabove, wettable powders and flowables may be used because they may be dispersed in water. Preferably, such flowables will be applied at the locus with the aqueous compositions being sprayed on the foliage of plants to be protected. These sprays also may be applied to the breeding ground, food supply or habitat of the insects and acarina sought to be controlled Where solid formulations of the compounds of this invention are to be used in combination treatments with other pesticidal agents, the formulations can be applied as an admixture of the components or may be applied sequentially.

Similarly, liquid formulations of the bis- and tris(trifluoromethyl)arylpyrroles in combination with other pesticidal agents may be tank mixed or may be applied separately, sequentially, as liquid sprays. Liquid spray formulations of the compounds of the invention should contain about 0.001% to 0.1% by weight of the active bis- or tris(trifluoromethyl)arylpyrrole.

In order to facilitate a further understanding of the invention, the following examples are presented primarily for the purpose of illustrating more specific details thereof. The invention is not to be deemed limited thereby except as defined in the claims.

EXAMPLE 1

Preparation of p-Chloro-0-[1,2-bis(trifluoromethyl)-vinyl]acetophenone oxime, vinyl-(Z) and 2-(p-chlorohenyl)-4.5-trans-bis(trifluoromethyl)-1-pyrrolin-5-ol

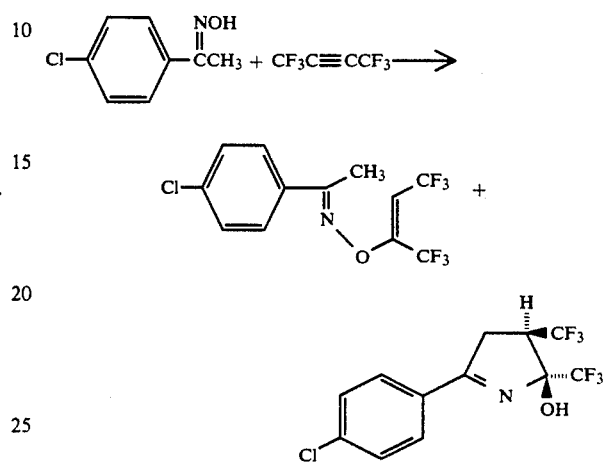

Hexafluoro-2-butyne is slowly bubbled through a 55°–60° C. solution of p-chloroacetophenone oxime (17.0 g, 0.10 mol), methanol (80 mL) and potassium tert-butoxide (1.12 g, 0.01 mol) over a 5 hour period. The solvent is removed in vacuo to obtain a liquid which is poured into water and extracted with ether. The combined organic extracts are washed sequentially with water and brine, dried over anhydrous sodium sulfate and concentrated in vacuo to give an oil. The oil is chromatographed using silica gel and eluted with ethylacetate in methylene chloride to 5% ethyl acetate in methylene chloride to give p-chloro-0-[1,2-bis(trifluoromethyl)vinyl]acetophenone oxime, vinyl-(Z) as a yellow liquid (21.5 g, 65%) and 2-(p-chlorophenyl)-4,5-trans-bis(trifluoromethyl)-1-pyrrolin-5-ol as a white solid (2.35 g, mp 152.5°–153° C., 7%).

Following the procedure of example 1, but substituting the appropriately substituted acetophenone oxime yields the following compounds.

| L | M | Q | mp °C. |
|---|---|---|---|
| H | 4-CF$_3$ | H | |
| H | 4-Cl | 3-Cl | |
| H | H | H | |

-continued

| L | M | Q | mp °C. |
|---|---|---|---|
| H | 3-Cl | 4-Cl | 147-148 |

EXAMPLE 2

Preparation of
2-(p-chlorophenyl)-4,5-bis-(trifluoromethyl)-1-pyrrolin-4-ol,trans- and cis-

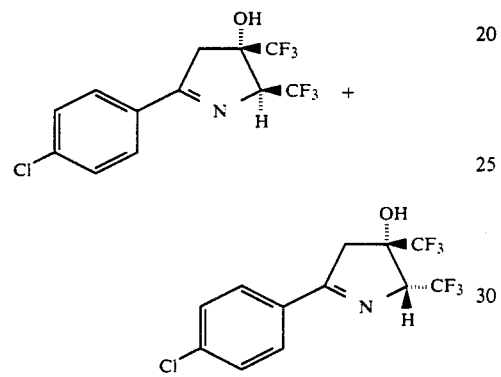

A solution of p-chloro-O-[1,2-bis(trifluoromethyl)-vinyl]acetophenone oxime, vinyl-(Z) (10.0 g, 0.03 mol) and xylene (50 mL) is heated at reflux temperature for 2½ hours. The solvent is removed in vacuo to give a semi-solid. The semi-solid is crystallized from a chloroform/hexanes mixture to give 2-(chlorophenyl)-4,5-bis(-trifluoromethyl)-1-pyrrolin-4-ol, trans- as a white solid (3.7 g, mp 111.0°-111.5° C., 37%). The filtrate is concentrated in vacuo to give an oil which is chromatographed using silica gel and eluted with 1% and 3% ethyl acetate in methylene chloride to give additional 2-(p-chlorophenyl)-4,5-bis(trifluoromethyl)-1-pyrrolin-4-ol,trans- (0.20 g) and 2-(p-chlorophenyl)-4,5-bis(trifluoromethyl)-1-pyrrolin-4-ol,cis- as a white solid (0.95 g, mp 99°-101° C., 9.5%).

Following the procedure of example 2 but substituting the appropriately substituted O-[1,2-bis(trifluoromethyl)vinyl]aceophenone, oxime for p-chloro-O-[ 1,2-bis(-trifluoromethyl)vinyl]acetophenone, oxime yields the following compounds.

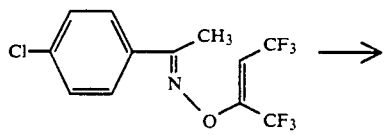

| L | M | Q | mp °C. |
|---|---|---|---|
| H | 4-CF$_3$ | H | 115.5-116.5 |
| H | 3-Cl | 4-Cl | oil |
| H | H | H | |
| H | 4-CF$_3$ | H | |
| H | 3-Cl | 4-Cl | oil |

EXAMPLE 3

Preparation of
5-(p-Chlorophenyl)-2,3-bis(trifluoromethyl)pyrrole

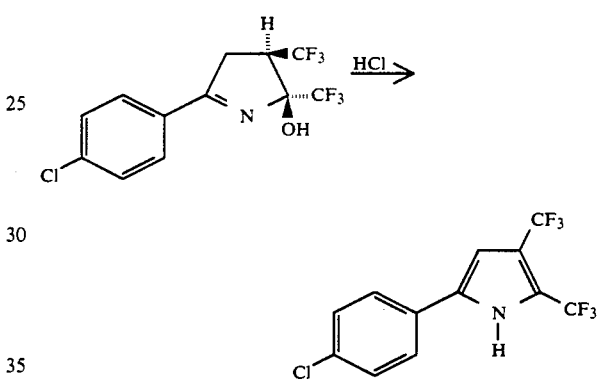

To ethanol (12mL) saturated with hydrochloric acid gas is added 2-(p-chlorophenyl)-4,5-trans-bis(trifluoromethyl)-1-pyrrolin-5-ol (1.2 g, 3.6 mmol). The reaction mixture is refluxed for 15 minutes, diluted with water and extracted with ether. The combined organic extracts are washed sequentially with water and brine, dried over anhydrous sodium sulfate and concentrated in vacuo to give a solid. Crystallization of the solid from hexanes gives the title product as a white solid (0.94 g, mp 72°-73° C., 83%).

Following the procedure of example 3, but substituting the appropriately substituted 2-aryl-4,5-bis(trifluoromethyl)-1-pyrrolin-5-ol or 2-aryl-4,5-bis-(trifluoromethyl)-1-pyrrolin-4-ol for 2-(p-chlorophenyl)-4,5-trans-bis(trifluoromethyl)-1-pyrrolin-5-ol yields the following compounds.

| L | M | Q | mp °C. |
|---|---|---|---|
| H | H | H | 61.0-61.5 |
| H | 3-Cl | 4-Cl | 51.5-53.0 |
| H | 4-CF$_3$ | H | 43-44 |

EXAMPLE 4

Preparation of
3-Bromo-2-(p-chlorophenyl)-4,5-bis(trifluoromethyl)-pyrrole

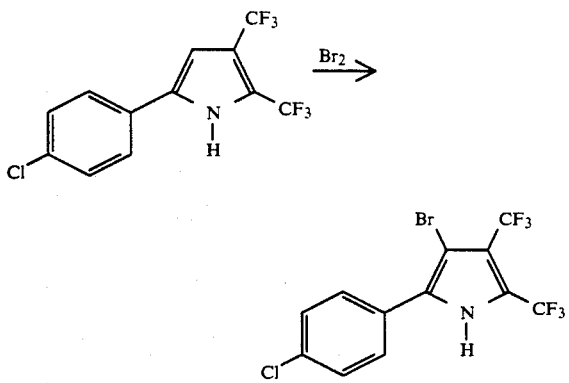

Bromine (0.527 g, 3.3 mmol) is added to a room temperature solution of 5-(p-chlorophenyl)-2,3-bis(trifluoromethyl)pyrrole (0.9 g, 3.0 mmol), acetic acid (5 mL) and sodium acetate (0.492 g, 6 mmol). After stirring for 2 hours the reaction mixture is diluted with water and extracted with ether. The combined organic extracts are washed sequentially with water, sodium metabisulfite solution, water and brine, dried over anhydrous magnesium sulfate and concentrated in vacuo to obtain a solid. Crystallization of the solid from hexanes gives the title product as white crystals (0.77 g, mp 64.5°–65.0° C., 65%).

Following the procedure of example 4, but substituting the appropriate 5-aryl-2,3-bis(trifluoromethyl)pyrrole for 5-(p-chlorophenyl)-2,3-bis(trifluoromethyl)pyrrole yields the following compounds.

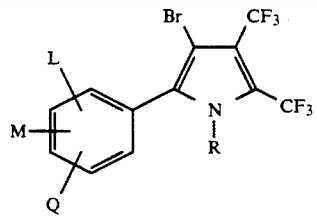

| L | M | Q | mp °C. |
|---|---|---|---|
| H | 3-Cl | 4-Cl | 84.5–86 |
| H | 4-CF$_3$ | H | 76.5–79 |

EXAMPLE 5

Preparation of
3-Bromo-2-(3,4-dichlorophenyl)-1-(ethoxymethyl)-4,5-bis(trifluoromethyl)pyrrole

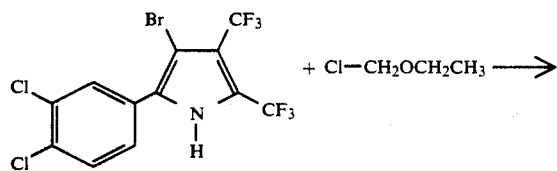

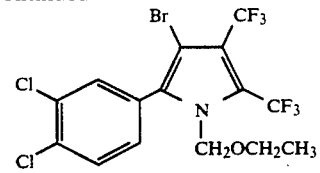

To a chilled solution of 3-bromo-2-(3,4-dichlorophenyl)-4,5-bis(trifluoromethyl)pyrrole (0.854 g, 2 mmol) and tetrahydrofuran is added potassium tert-butoxide (0.247 g, 2.2 mmol). After stirring at ice bath temperature for 15 minutes chloromethyl ethyl ether (0.208 g, 2.2 mmol) is added to the reaction mixture and the ice bath is removed. Stirring is continued for 1 ½ hours then the reaction mixture is diluted with water and extracted with ether. The combined organic extracts are washed sequentially with water and brine, dried over anhydrous sodium sulfate and concentrated in vacuo to give the title compound as a yellow liquid (0.91 g, 94%). Identified by IR and NMR spectral analyses.

Following the procedure described in example 5, but using the appropriately substituted 3-bromo-2-phenyl-4,5-bis(trifluoromethyl)pyrrole and the appropriate alkylating or cyanating agent, the compounds shown below are obtained.

| R | L | M | Q | mp °C. |
|---|---|---|---|---|
| CH$_2$OCH$_2$CH$_3$ | H | 4-CF$_3$ | H | oil |
| C≡N | H | 4-Cl | H | 113.5–114.5 |
| CH$_3$ | | | | |
| w | | | | |
| CH—O—CH(CH$_3$)$_2$ | H | 4-Cl | 3-Cl | oil |
| CH$_3$ | H | 3-Cl | 4-Cl | 101–103.5 |
| CH$_2$OCH$_2$CH$_3$ | H | 4-Cl | H | 48–49 |
| C≡N | H | 3-Cl | 4-Cl | 71.5–72.5 |

EXAMPLE 6

Preparation of 3-Bromo-1,1,1-trifluoro-2-propanone, oxime

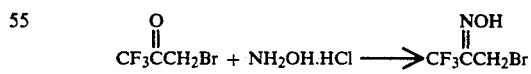

A solution of hydroxylamine hydrochlo (13.9 g, 0.2 mol) and methanol (100 mL) is added at room temperature over 30 minutes to 3-bromo-1,1,1-trifluoropropanone (38.2 g, 0.2 mol) and stirred for 2 days. The solvent is removed in vacuo to give an liquid. The liquid is diluted with water and extracted with methylene chloride. The combined organic extracts are washed sequentially with water and brine, dried over anhydrous sodium sulfate and concentrated in vacuo to obtain a liquid. Vacuum distillation of the liquid gives the title

EXAMPLE 7

Preparation of
3-(p-Chlorophenyl)-1,1,1,6,6,6-hexafluoro-2,5-hexanedione, 5-oxime

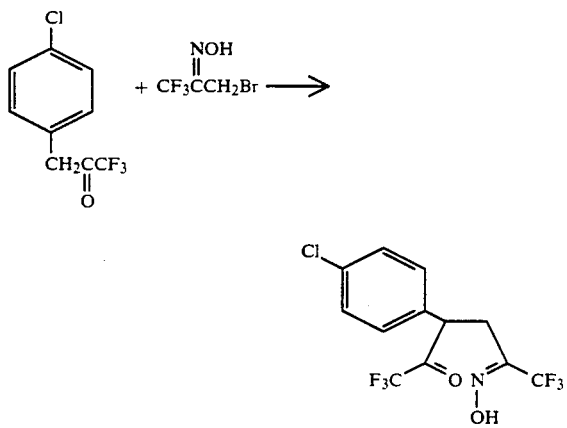

product as a colorless liquid (20.0 g, bp 50°–54° C., 7.5mm, 49%).

A solution of 3-(p-chlorophenyl)-1,1,1-trifluoro-2-propanone (8.9 g, 0.04 mol) and tetrahydrofuran (25 mL) is added dropwise over fifteen minutes to a solution of potassium tert-butoxide (4.93 g, 0.044 mol) and tetrahydrofuran (50 mL) under a nitrogen blanket. The reaction mixture heats up to 35° C. during the addition. After stirring for 15 minutes a solution of 3-bromo-1,1,1-trifluoro-2-propanone, oxime (8.24 g, 0.04 mol) and tetrahydrofuran (20 mL) is added dropwise to the reaction mixture and the temperature of the reaction mixture rises to 35°. After 1½ hours the reaction mixture is diluted with water and extracted with ether. The combined organic extracts are washed sequentially with water and brine, dried over anhydrous sodium sulfate and concentrated in vacuo to obtain an oil. Crystallization of the oil from hexanes gives the title product as a white solid (9.0 g, mp 106.5°–107.5° C., 65%).

EXAMPLE 8

Preparation of
3-(p-Chlorophenyl)-2,5-bis(trifluoromethyl)-1-hydoxypyrrole

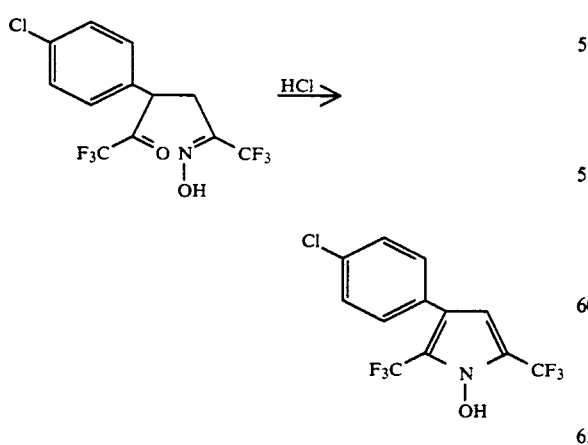

A solution of 3-(p-chlorophenyl)-1,1,1,6,6,6-hexafluoro-2,5-hexanedione,5-oxime (17.1 g, 0.049 mol) and ethanol saturated with hydrochloric acid gas is refluxed for forty minutes. The reaction mixture is diluted with water and extracted with ether. The combined organic extracts are washed sequentially with water and brine, dried over anhydrous sodium sulfate and concentrated in vacuo to obtain a liquid. Vacuum distillation of the liquid gives the title compound as a pale yellow viscous liquid (12.9g, bp 82°–95° C./0.2 mm, 80%).

EXAMPLE 9

Preparation of
3-(p-Chlorophenyl)-2,5-bis(trifluoromethyl)pyrrole

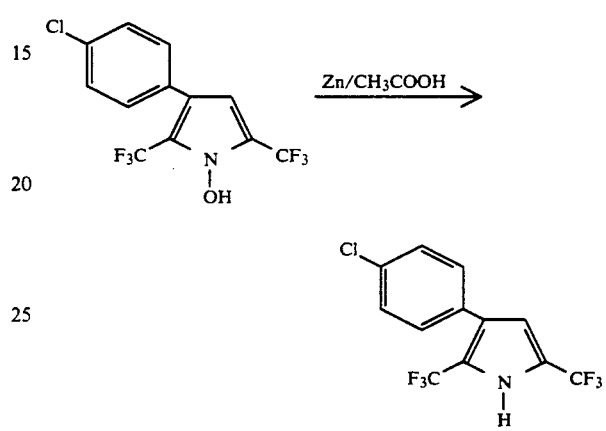

Zinc dust (20 g, 0.3 mol) is added to a solution of 3-(p-chlorophenyl)-2,5-bis(trifluoromethyl)-1-hydroxypyrrole (7.5 g, 0.023 mol) and acetic acid (50 mL). The reaction mixture is refluxed for ½ hour, cooled to room temperature, filtered to remove solids, diluted with water and extracted with ether. The combined organic extracts are washed sequentially with water, sodium carbonate solution and brine, dried over anhydrous magnesium sulfate and concentrated in vacuo to give a pale red liquid (6.8 g). A portion of the red liquid (1.6 g) is chromatographed using silica gel and eluted with methylene chloride to give the title product as a colorless liquid (1.1 g). Identified by IR and NMR spectral analyses.

EXAMPLE 10

Preparation of
3-Bromo-4-(p-chlorophenyl)-2,5-bis(trifluoromethyl)-pyrrole

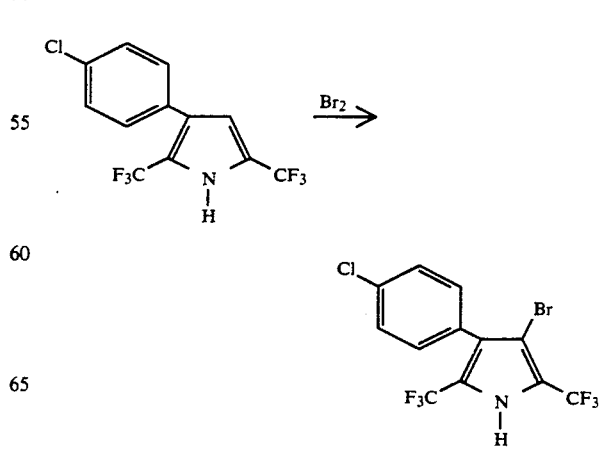

Bromine (0.527 g, 0.17 mL, 0.0033 mol) is added to a solution of 3-(p-chlorophenyl)-2,5-bis(trifluoromethyl)-pyrrole (0.94 g, 0.003 mol), acetic acid (6 mL) and sodium acetate (0.984 g, 0.012 mol). After 1 hour the reaction mixture is diluted with water and extracted with ether. The combined organic extracts are washed sequentially with water, sodium metabisulfite solution, water and brine, dried over anhydrous sodium sulfate and concentrated in vacuo to give a colorless oil. The oil is chromatographed using silica gel and eluted with methylene chloride to give the title compound as a colorless oil (0.4 g, 34%). Identified by IR and NMR spectral analyses.

EXAMPLE 11

Preparation of
3-(p-Chlorophenyl)-1,1,1-trifluoro-2-propanone

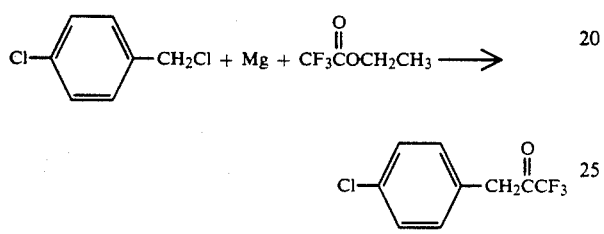

A solution of p-chlorobenzyl chloride (80.5 g, 0.5 mol) and ether (150 mL) is slowly added to a vigorously stirred slurry of magnesium turnings (12.15 g, 0.5 mol) and ether (50 mL) over a 45 minute period. After the addition is complete, the reaction mixture is refluxed for ½ hour then cooled in an ice bath. The Grignard reagent is then added to a solution of ethyl trifluoroacetate (71.04 g, 0.5 mol) and ether (150 mL) at −60° to −70° C. (acetone-dry ice bath) over a 45 minute period. The cooling bath is removed and the reaction mixture is allowed to warm to −10° C. The reaction mixture is then quenched with saturated ammonium chloride solution and then acidified with 10% hydrochloric acid solution. The organic layer is separated, washed sequentially with water and brine, dried over anhydrous magnesium sulfate and concentrated in vacuo to obtain a liquid. Vacuum distillation of the liquid gives the title product as a clear liquid (52.8 g, bp 72°-74° C./34 mm, 47%).

EXAMPLE 12

Preparation of
3-(p-Chlorophenyl)-1,1,1-trifluoro-2-propanone oxime

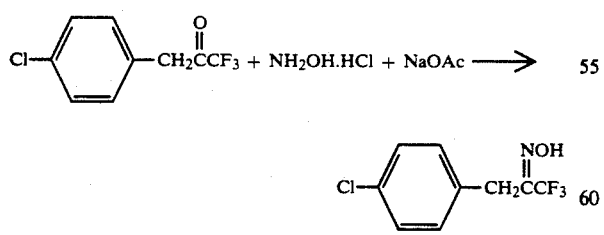

A solution of 3-(p-Chlorophenyl)-1,1,1-trifluoro-2-propanone (10.0 g, 0.045 mol) and ethanol (60 mL) is treated with a solution of hydroxylamine hydrochloride (4.68 g, 0.067 mol) and water (20 mL) and then with a solution of sodium acetate (5.53 g, 0.067 mol) and water (20 mL). The reaction mixture is then refluxed for 2 hours, cooled to room temperature, diluted with water and extracted with ether. The combined organic extracts are washed sequentially with water and brine, dried over anhydrous sodium sulfate and concentrated in vacuo to give a liquid which solidifies upon standing to give the title product as white needles (11.84 g). Identified by IR and NMR spectral analyses.

EXAMPLE 13

Preparation of
3-(p-Chlorophenyl)-5a-hydroxy-2,4-a,5b-tris(trifluoromethyl)-1-pyrroline

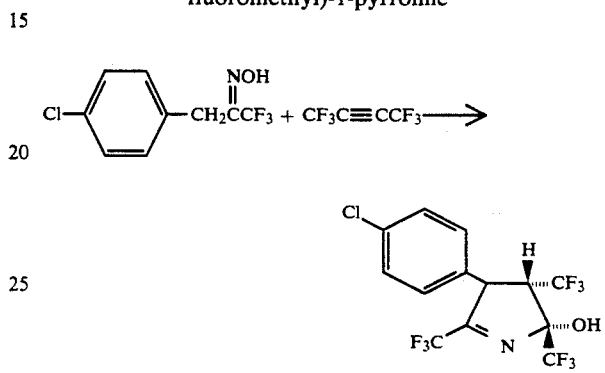

A solution of 3-(p-chlorophenyl)-1,1,1-trifluoro-2-propanone oxime (7.13 g, 0.03 mol), potassium tert-butoxide (0.337 g, 0.003 mol) and methanol (25 mL) in a pressure bottle is cooled in an acetone dry ice bath and treated with previously condensed liquid hexafluoro-2-butyne (30 g). The pressure bottle is then sealed and the reaction mixture is heated to 60°-70° C. over a 90 minute period. The pressure rises to 100 psi and after ½ hour drops slowly to about 15-20 psi. The reaction mixture is then allowed to stand at room temperature overnight, poured into water and extracted with ether. The combined organic extracts are washed sequentially with water and brine, dried over anhydrous sodium sulfate and concentrated in vacuo to give an oil. Chromatography of the oil using silica gel and 3% ethylacetate in methylene chloride as eluant gives 3-(p-chlorophenyl)-1,1,1-trifluoro-0-[3,3,3-trifluoro-1-(trifluoromethyl)-propenyl]-2-propanone, oxime, vinyl-,(E)- as a yellow liquid (8.5 g, 71%) and the title product as a yellow syrup (0.46 g, 4%). Identified by IR and NMR spectral analyses.

EXAMPLE 14

Preparation of
3-(p-Chlorophenyl)-2,4,5-tris(trifluoromethyl)pyrrole

-continued

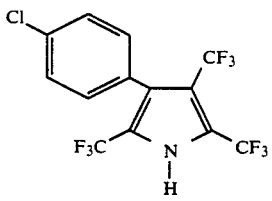

3-(p-Chlorophenyl)-5a-hydroxy-2,4-a,5b-tris(trifluoromethyl)-1-pyrroline (0.4 g, 1 mmol) is dissolved into ethanol (8 mL) saturated with hydrochloric acid gas and the resulting solution is refluxed for 1 ½ hours. The reaction mixture is diluted with water and extracted with ether. The combined organic extracts are washed sequentially with water and brine, dried over anhydrous magnesium sulfate and concentrated in vacuo to give an oil. Chromatography of the oil using silica gel and methylene chloride as eluant give the title product as a colorless liquid (0.13 g, 34%). Identified by IR and NMR spectral analyses.

EXAMPLE 15

Preparation of 4-(p-Chlorophenyl)-2-trifluoromethyl-2-oxazolin-5-one

In a single portion, trifluoroacetic anhydride, (1.7 mL; 0.012 mol) is added to powdered 2-(p-chlorophenyl)glycine (11.4 g; 0.06 mol), causing an immediate exotherm to about 40° C., a yellow color forms on the surface of the solid. As the mixture is slowly heated to 70° C., more of the solid dissolves to an orange/amber oil. All the solid dissolves in approximately 2 hours, and heating is continued another hour. Solvent is removed under reduced pressure on a rotary evaporator. Toluene is twice added and removed under reduced pressure, but the odor of trifluoroacetic acid is still evident. This yellow semi-solid (yield theoretical; purity >90% by HPLC) is the above-identified compound and is used in the next step without further purification.

EXAMPLE 16

Preparation of 2-(p-Clorophenyl)-3,5-bis(trifluoromethyl)pyrrole

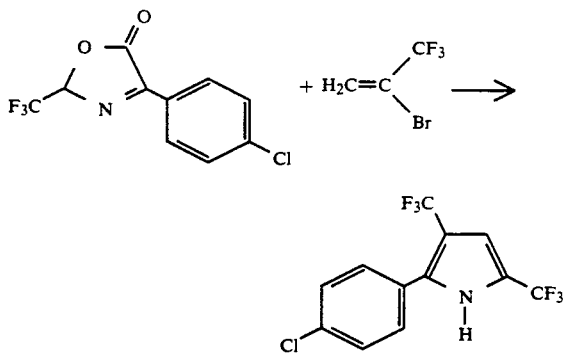

A solution of 3.0 g of 4-p-chlorophenyl-2-trifluoromethyl-oxazolin-5-one, 2.0 g of 2-bromo-3,3,3-trifluoropropene and acetonitrile is treated with 1.2 g of triethylamine, heated at reflux temperature for one hour, and concentrated in vacuo to give a residue. The residue is chromatographed on silica gel using a 4:1 mixture of hexane:ethyl acetate to give the title compound as a colorless solid, 1.6 g mp 41°–43° C.

EXAMPLE 17

Preparation of 3-Bromo-5-(p-chlorophenyl)-2,4-bis(trifluoromethyl)-pyrrole

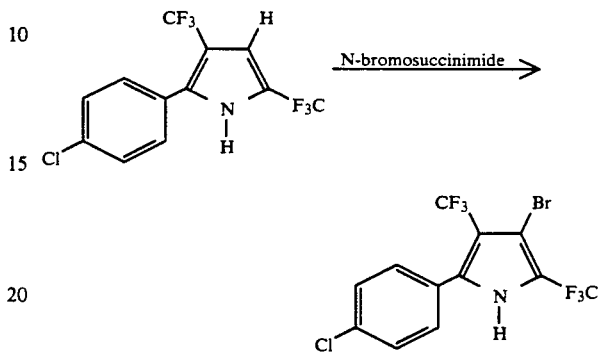

N-Bromosuccinimide (0.9 g, 5 mmol) is added to a solution of 2-(p-chlorophenyl)-3,5-bis(trifluoromethyl)-pyrrole (0.78 g, 2.5 mmol) and tetrahydrofuran (50 mL). The reaction mixture is stirred at room temperature overnight then concentrated in vacuo to give a solid. The solid is chromatographed using silica gel and 20% ethyl acetate in hexanes as eluant to yield the title compound as a light green solid (0.376 g, mp 71°–75° C., 38%).

EXAMPLE 18

Preparation of 2-(p-Chlorophenyl)-3,4-bis(trifluoromethyl)pyrrole

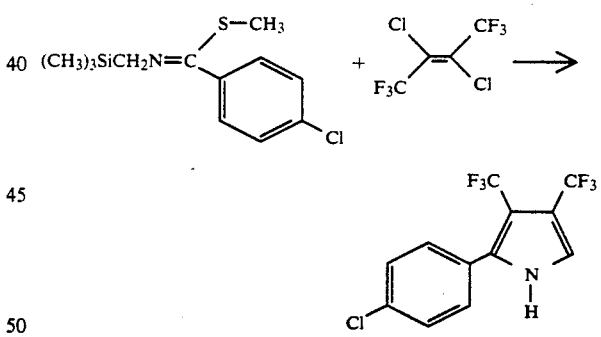

Under a nitrogen purge, methyl p-chlorothio-N-[(trimethylsilyl)methyl]benzimidate (2.7 g, 0.01 mol) is dissolved in hexamethylphosphoramide (HMPA, 15 mL) to form a clear solution. In a single portion, 2,3-dichloro-hexafluorobutene (2.3 g, 0.01 mol) is added, washed in with a 10 mL portion of HMPA. Water (0.55 mL, 0.03 mol) is then added, washed in with 5 mL of HMPA, causing a slight exotherm. When the exotherm subsides the clear solution is heated gently with a heat gun, first to 45° C., then to 60° C., whereupon a spontaneous exotherm occurs, bringing the reaction mixture temperature to 85° C. The resulting red solution is allowed to cool to room temperature and stirred for 16 hours. The reaction mixture is then poured onto ice/water, filtered, washed with cold water and dried on the filter. Recrystallization of the solid from hexanes gives the title product as white crystals as a solvate with 0.5 mole of HMPA (1.3 g, mp 117°-119° C., 33%). Identified by IR and spectral analyses.

EXAMPLE 19

Preparation of 2-Bromo-5-(p-chlorophenyl)-3,4-bis(trifluoromethyl)-pyrrole

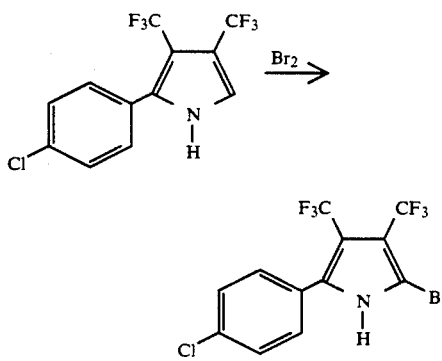

Under a nitrogen purge, a solution of bromine (0.05 mL, 0.001 mol) and chloroform (5 mL) is added dropwise to a solution of 2-(p-chlorophenyl)-3,4-bis(trifluoromethyl)pyrrole (0.39 g, 0.001 mol) and chloroform (10 mL). The orange reaction mixture is stirred for 16 hours at room temperature then concentrated in vacuo to give an oil. The oil is extracted with methyl cyclohexane and the combined organic extracts are treated with carbon black and the solvent is removed in vacuo. The residue is dissolved in a small amount of hot hexane, decanted from insolubles and cooled in the freezer. Filtration of the cold solution gives the title compound as white crystals containing a half mole of HMPA (0.32 g mp 97°-100° C., 68%). Identified by IR and NMR spectral analyses.

EXAMPLE 20

Insecticide and acaricide evaluations

The following tests show the efficacy of the compounds as insecticides and acaricides All tests are performed using technical materials and kept at 27° C. The test concentrations are in terms of active ingredient.

*Spodoptera eridania*, 3rd instar larvae, southern armyworm

A sieva lima bean leaf expanded to 7 to 8 cm in length is dipped in the test suspension with agitation for 3 seconds and placed in a hood to dry. The leaf is then placed in a 100×10 mm petri dish containing a damp filter paper on the bottom and 10 3rd instar caterpillars. The dish is maintained for 5 days before observations are made of mortality, reduced feeding, or any interference with normal moulting.

*Spodoptera eridania*, 7-day residual

The plants treated in the above test are maintained under high intensity lamps in the greenhouse for 7 days. These lamps duplicate the effects of a bright sunny day in June in New Jersey and are kept on for 14 hour day length. After 7 days, the foliage is sampled and assayed as in the above-said test.

*Alphis fabae*, mixed instar, bean aphid

Pots containing single nasturtium plants (Trocaeolum sp.) about 5 c tall are infested with about 100 to 200 aphids one day before the test. Each pot is sprayed with the test formulation for 2 revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and held for 2 days, following which mortality estimates are made.

*Tetranychus urticae* (P-resistant strain), 2-spotted spider mite

Sieva lima bean plants with primary leaves expanded to 7 to 8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test formulation for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

*Diabrotic undecimpunctata howardi*, 3rd instar southern corn rootworm

One cc of fine talc is placed in a 30 mL wide-mouth screw-top glass jar. One mL of the appropriate acetone suspension is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, 10 3rd instar rootworms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 and 10 kg/ha, respectively.

| Rating Scale: | |
|---|---|
| 0 = no effect | 5 = 56 to 65% kill |
| 1 = 10 to 25% kill | 6 = 66 to 75% kill |
| 2 = 26 to 35% kill | 7 = 76 to 85% kill |
| 3 = 36 to 45% kill | 8 = 86 to 99% kill |
| 4 = 46 to 55% kill | 9 = 100% kill |

The data obtained for the above-described evaluations are reported in Table I.

TABLE I

| Insecticide And Acaricide Evaluations | | | | | |
|---|---|---|---|---|---|
| | BEAN | Southern Armyworm | | P. RES | |
| | APHIDS | | Residual | MITES | SCRW[1] |
| | (ppm) | (ppm) | (ppm) | 7 days, | (ppm) | (kg/ha) |

TABLE I-continued

Insecticide And Acaricide Evaluations

| Compound | 100 | 1000 | 100 | 1000 ppm | 300 | 50 |
|---|---|---|---|---|---|---|
| 2-bromo-5-(p-chlorophenyl)-3,4-bis-(trifluoromethyl)pyrrole | 9 | 9 | 9 | 9 | 9 | 0 |
| 3-bromo-2-(p-chorophenyl)-4,5-bis-(trifluoromethyl)pyrrole-1-carbonitrile | 9 | 9 | 9 | 9 | 9 | 8 |
| 3-bromo-2-(p-chlorophenyl)-1-(ethoxymethyl)-4,5-bis(trifluoromethyl)pyrrole | 0 | 9 | 9 | 9 | 0 | 9 |
| 3-bromo-2-(p-chorophenyl)-4,5-bis-(trifluoromethyl)pyrrole | 9 | 9 | 9 | 9 | 9 | 9 |
| 3-bromo-5-(p-chlorophenyl)-2,4-bis-(trifluoromethyl)pyrrole | 0 | 9 | 9 | 9 | 9 | 0 |
| 3-(p-chlorophenyl)-2,4,5-tris(trifluoromethyl)pyrrole | 0 | 9 | 9 | 0 | 9 | 9 |
| 3-bromo-2-(3,4-dichlorophenyl)-4,5-bis(trifluoromethyl)pyrrole | 9 | 9 | 9 | 9 | 9 | 9 |
| 3-bromo-2-(3,4-dichlorophenyl)-4,5-bis(trifluoromethyl)pyrrole-1-carbonitrile | 9 | 9 | 9 | 9 | 9 | 9 |

| | BEAN APHIDS | Southern Armyworm | | | P. RES MITES | SCRW[1] |
|---|---|---|---|---|---|---|
| Compound | (ppm) 100 | (ppm) 1000 | (ppm) 100 | 7 days | (ppm) 300 | (kg/ha) 50 |
| 3-bromo-2-(3,4-dichlorophenyl)-1-(ethoxymethyl)-4,5-bis(trifluoromethyl)pyrrole | 9 | 9 | 9 | 9 | 0 | 9 |
| 3-bromo-4-(p-chorophenyl)-2,5-bis-(trifluoromethyl)pyrrole | 0 | 9 | 0 | — | 9 | 9 |
| 3-bromo-2-(3,4-dichlorophenyl)-1-methyl-4,5-bis(trifluoromethyl)pyrrole | 8 | 9 | 0 | 9 | 0 | 0 |
| 3-bromo-2-(3,4-dichlorophenyl)-1-(1-isopropoxyethyl)-4,5-bis(trifluoromethyl)pyrrole | 8 | 9 | 9 | 9 | 9 | 9 |
| 3-bromo-4,5-bis(trifluoromethyl)-2-(alpha, alpha, alpha-trifluoro-p-tolyl)pyrrole | 6 | 9 | 9 | 9 | 9 | 9 |
| 3-bromo-1-(ethoxymethyl)-4,5-bis(trifluoromethyl)-2-(alpha, alpha, alpha-trifluoro-p-tolyl)pyrrole | 0 | 9 | 9 | 0 | 0 | 9 |

[1]SCRW designates southern corn rootworm

The above test results show the efficacy of the compounds as insecticides and acaricides.

EXAMPLE 21

The following tests show the efficacy of the compounds as insecticides. All tests are performed using technical materials and kept at 27° C. The test concentrations are in terms of active ingredient.

*Heliothis virescens*, 3rd instar tobacco budworm

Cotton cotyledons are dipped in the test formulation and allowed to dry in a hood. When dry, each is cut into quarters and ten sections placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Empoasca abrupta*, adults, western potato leafhopper

A Sieva lima bean leaf about 5 cm long is dipped in the test formulation for 3 seconds with agitation and placed in a hood to dry. The leaf is placed in a 100×10 mm petri dish containing a moist filter paper on the bottom. About 10 adult leafhoppers are added to each dish and the treatments are kept for 3 days before mortality counts are made.

*Blattella germanica*, bait test, adult male German cockroach

A 0.1% bait is prepared by pipetting 1 mL of a 1000 ppm solution of the test compound in acetone onto 1 gram of cornmeal in a 30 mL wide-mouth bottle. The bait is dried by passing a gentle stream of air into the bottle. The bait is placed in a 1 pint wide-mouth Mason jar and 10 adult male cockroaches are added. A screen lid is placed on the jar and a small piece of cotton soaked in 10% honey is put on the top of the screen lid. Mortality counts are made after 3 days.

*Blattella cermanica*, residue test, adult male German cockroach

One mL of a 1000 ppm acetone solution of the test material is pipetted slowly over the bottom of a 150×15 mm petri dish so as to give as uniform coverage as possible. After the deposit has dried, 10 adult male cockroaches are placed in each dish and the lid is added. Mortality counts are made after 3 days.

*Spodoptera eridania*, systemic uptake, 3rd instar larvae, southern armyworm

The compound is formulated as an emulsion containing 0.1 gm of the test material, 0.2 gm of Emulphor EL-620 ® emulsifier, 10 mL of acetone and 90 mL of water. This is diluted 10-fold with water to give a 100 ppm emulsion for the test. Subsequent 10-fold dilutions are made with water as needed. Sieva lima bean plants, with the primary leaves expanded to a length of 7 to 8 cm, are cut off at least 3 cm above the soil level to avoid contamination with soil bacteria that will cause decay of the stem during the test. The cut stems are placed in the test emulsions and each stem is wrapped with a bit of cotton to hold the stem off the bottom of the bottle and to limit evaporation and volatilization of the compound. The test is maintained for 3 days at 27° to allow the compounds to be taken up into the plant. Following this, one leaf is removed from the plant and placed in a 100×10 mm petri dish with 10 southern armyworms. Mortality counts and observations of feeding damage are made 3 and 5 days later.

*Empoasca abrupta*, adults, western potato leafhoppers, systemic uptake

The compound is formulated as an emulsion containing 0.1 gm of the test material, 0.2 gm of Emulphor EL-620 ® emulsifier, 10 mL of acetone and 90 mL of water. This is diluted 10 fold with water to give a 100 ppm emulsion for the test. Subsequent 10-fold dilutions are made with water as needed. Sieva lima bean plants, with the primary leaves expanded to a length of 7 to 8 cm, are cut off at least 3 cm above the soil level to avoid contamination with soil bacteria that will cause decay of the stem during the test. The cut stems are placed in the test emulsion and each stem is wrapped with a bit of cotton to hold the stem off the bottom of the bottle and to limit evaporation and volatilization of the compound. The test is maintained for 3 days at 27° C. to allow the compounds to be taken up into the plant. Following this, one leaf is removed from the plant and placed in a 100×10 mm petri dish with 10 adult western potato leafhoppers. After 3 days, mortality counts are made.

The rating scale for the above evaluations is the same as described in Example 20.

The data obtained are reported in Table II.

TABLE II

Insecticide Evaluations

| Compound | LEAF HOPPER (ppm) 100 | Tobacco Budworm (ppm) 1000 | Tobacco Budworm (ppm) 100 | G. COCKROACH Bait (ppm) 1000 | G. COCKROACH Res (ppm) 1000 |
|---|---|---|---|---|---|
| 2-bromo-5-(p-chlorophenyl)-3,4-bis(trifluoromethyl)pyrrole | 9 | 9 | 4 | 9 | 9 |
| 3-bromo-2-(p-chlorophenyl)-4,5-bis-(trifluoromethyl)pyrrole-1-carbonitrile | 9 | 9 | 8 | 9 | 9 |
| 3-bromo-2-(p-chlorophenyl)-1-(ethoxymethyl)-4,5-bis(trifluoromethyl)pyrrole | 9 | 9 | 9 | 9 | 9 |
| 3-bromo-2-(p-chlorophenyl)-4,5-bis(trifluoromethyl)pyrrole | 9 | 9 | 9 | 9 | 9 |
| 3-bromo-5-(p-chlorophenyl)-2,4-bis(trifluoromethyl)pyrrole | 0 | 9 | 9 | 9 | 9 |
| 3-(p-chlorophenyl)-2,4,5-tris(trifluoromethyl)pyrrole | 9 | — | 9 | — | 9 |
| 3-bromo-2-(3,4-dichlorophenyl)-4,5-bis(trifluoromethyl)pyrrole | 9 | 9 | 9 | 0 | 9 |
| 3-bromo-2-(3,4-dichlorophenyl)-4,5-bis-(trifluoromethyl)pyrrole-1-carbonitrile | 9 | 9 | 9 | 0 | 9 |
| 3-bromo-2-(3,4-dichlorophenyl)-1-(ethoxymethyl)-4,5-bis(trifluoromethyl)pyrrole | 9 | 9 | 9 | 0 | 9 |
| 3-bromo-4-(p-chlorophenyl)-2,5-bis(trifluoromethyl)pyrrole | 9 | 5 | 0 | 0 | 9 |
| 3-bromo-2-(3,4-dichlorophenyl)-1-methyl-4,5-bis(trifluoromethyl)pyrrole | 8 | 0 | 0 | 0 | 9 |
| 3-bromo-2-(3,4-dichlorophenyl)-1-(1-isopropoxyethyl)-4,5-bis(trifluoromethyl)-pyrrole | 9 | 9 | 9 | 4 | 9 |
| 3-bromo-4,5-bis(trifluoromethyl)-2-(alpha, alpha, alpha-trifluoro-p-tolyl)pyrrole | 9 | 9 | 9 | 0 | 9 |
| 3-bromo-1-(ethoxymethyl)-4,5-bis(trifluoromethyl)-2-(alpha, alpha, alpha-trifluoro-p-tolyl)pyrrole | 8 | 0 | 0 | 0 | 9 |

What is claimed is:

1. A compound having the structure

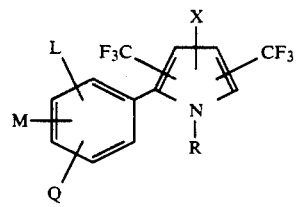

wherein
L is H, F, Cl or Br;
M and O are each independently H, F, Cl, Br, CN, NO$_2$, CF$_3$, C$_1$–C$_4$ alkyl or C$_1$–C$_3$ alkoxy;
X is Cl, Br, I or CF$_3$;
R is

hydrogen, cyano,
C$_1$–C$_6$ alkyl optionally substituted with one to three halogen atoms,
one tri(C$_1$–C$_4$ alkyl)silyl,
one hydroxy,
one cyano,
one or two C$_1$–C$_4$ alkoxy groups optionally substituted with one to three halogen atoms, one $C_1-C_4$ alkylthio,
one phenyl optionally substituted with one to three halogen atoms, one to three $C_1-C_4$ alkyl groups or one to three $C_1-C_4$ alkoxy groups,
one phenoxy group optionally substituted with one to three halogen atoms, one to three $C_1-C_4$ alkyl groups or one to three alkoxy groups,
one benxyloxy group optionally substituted on the phenyl ring with one to three halogen atoms, one to three $C_1-C_4$ alkyl groups or one to three $C_1-C_4$ alkoxy groups,
one $C_1-C_6$ alkylcarbonyloxy group optionally substituted with one to three halogen atoms,
one $C_2-C_6$ alkenylcarbonyloxy group optionally substituted with one to three halogen atoms,
one phenylcarbonyloxy group optionally substituted with one to three halogen atoms, one to three $C_1-C_4$ alkyl groups or one to three $C_1-C_4$ alkoxy groups,
one $C_1-C_6$ alkoxycarbonyl group optionally substituted with one to three halogen atoms or one to three $C_1-C_4$ alkoxy groups, or
one benzyloxycarbonyl group optionally substituted on the phenyl ring with one to three halogen atoms, one to three $C_1-C_4$ alkyl groups or one to three $C_1-C_4$ alkoxy groups,
$C_3-C_6$ alkenyl optionally substituted with one to three halogen atoms or one phenyl group, or
$C_3-C_6$ alkynyl optionally substituted with one to three halogen atoms or one phenyl group; and
$R_1$ is $C_1-C_6$ alkyl optionally substituted with one to three halogen atoms,
one hydroxy,
one cyano,
one or two $C_1-C_4$ alkoxy groups optionally substituted with one to three halogen atoms,
one $C_1-C_4$ alkylthio,
one phenyl optionally substituted with one to three halogen atoms, one to three $C_1-C_4$ alkyl groups or one to three $C_1-C_4$ alkoxy groups,
one phenoxy group optionally substituted with one to three halogen atoms, one to three $C_1-C_4$ alkyl groups or one to three $C_1-C_4$ alkoxy groups,
one benzyloxy group optionally substituted on the phenyl ring with one to three halogen atoms, one to three $C_1-C_4$ alkyl groups or one to three $C_1-C_4$ alkoxy groups,
one $C_1-C_6$ alkylcarbonyloxy group optionally substituted with one to three halogen atoms,
one $C_2-C_6$ alkenylcarbonyloxy group optionally substituted with one to three halogen atoms,
one phenylcarbonyloxy group optionally substituted with one to three halogen atoms, one to three $C_1-C_4$ alkyl groups or one to three $C_1-C_4$ alkoxy groups,
one $C_1-C_6$ alkoxycarbonyl group optionally substituted with one to three halogen atoms or one to three $C_1-C_4$ alkoxy groups, or
one benzyloxycarbonyl group optionally substituted on the phenyl ring with one to three halogen atoms, one to three $C_1-C_4$ alkyl groups or one to three $C_1-C_4$ alkoxy groups,
$C_3-C_6$ alkenyl optionally substituted with one to three halogen atoms or one phenyl group,
$C_3-C_6$ alkynyl optionally substituted with one to three halogen atoms or one phenyl group,
phenyl optionally substituted with one to three halogen atoms, one or two $C_1-C_4$ alkyl groups, one or two $C_1-C_4$ alkoxy groups, $CF_3$, CN, $NO_2$, di($C_1-C_4$ alkyl)amino or $C_1-C_4$ alkanoylamino,
phenoxy optionally substituted with one to three halogen atoms, one or two $C_1-C_4$ alkyl groups, one or two $C_1-C_4$ alkoxy groups, $CF_3$, CN, $NO_2$, di($C_1-C_4$ alkyl)amino or $C_1-C_4$ alkanoylamino,
$C_1-C_6$ alkoxy optionally substituted with one to three halogen atoms,
$C_2-C_6$ alkenyloxy optionally substituted with one to three halogen atoms,
di($C_1-C_4$ alkyl)amino, N-($C_1-C_4$ alkyl)-N-phenylamino or -N-halophenylamino, or
$C_3-C_6$ polymethyleneimino.

2. The compound according to claim 1, wherein
L is H, Cl, Br or F;
M and Q are each independently H, F, Cl, Br, CN, $NO_2$ or $CF_3$;
X is Cl, Br, I or $CF_3$;
R is

hydrogen, cyano or $C_1-C_6$ alkyl optionally substituted with one to three halogen atoms, CN, $C_1-C_4$ alkoxy, $C_1-C_6$ alkylcarbonyloxy or benzyloxycarbonyl; and
$R_1$ is phenyl optionally substituted with one to three halogen atoms.

3. The compound according to claim 2, 3-bromo-2-(3,4-dichlorophenyl)-4,5-bis(trifluoromethyl)pyrrole.

4. The compound according to claim 2, 3-bromo-2-(3,4-dichlorophenyl)-1-(1-isopropoxyethyl)-4,5-bis(trifluoromethyl)pyrrole.

5. The compound according to claim 2, 3-bromo-2-(p-chlorophenyl)-4,5-bis(trifluoromethyl)pyrrole.

6. The compound according to claim 2, 3-bromo-2-(3,4-dichlorophenyl)-4,5-bis(trifluoromethyl)pyrrole-1-carbonitrile.

7. The compound according to claim 2, 3-bromo-2-(3,4-dichlorophenyl)-1-(ethoxymethyl)-4,5-bis(trifluoromethyl)pyrrole.

8. A method for controlling insects and acarina which comprises contacting said insects or acarina, their breeding grounds, food supply or habitat with an insecticidally or acaricidally effective amount of a bis- or tris(trifluoromethyl)arylpyrrole compound having the formula

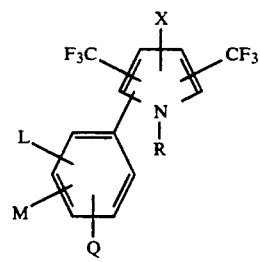

wherein
L is H, F, Cl or Br;
M and O are each independently H, F, Cl, Br, CN, $NO_2$, $CF_3$, $C_1-C_4$ alkyl or $C_1-C_3$ alkoxy; X is Cl, Br, I or $CF_3$;
R is

hydrogen, cyano, $C_1$-$C_6$ alkyl optionally substituted with one to three halogen atoms,
one tri($C_1$-$C_4$ alkyl)silyl,
one hydroxy,
one cyano,
one or two $C_1$-$C_4$ alkoxy groups optionally substituted with one to three halogen atoms,
one $C_1$-$C_4$ alkylthio,
one phenyl optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$ alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkylcarbonyloxy group optionally substituted with one to three halogen atoms,
one $C_2$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$C_6$ alkoxycarbonyl group optionally substituted with one to three halogen atoms or one to three $C_1$-$C_4$ alkoxy groups, or
one benzyloxycarbonyl group optionally substituted on the phenyl ring with one to three halogen atoms, one to three $C_1$-$C_4$ or one to three $C_1$-$C_4$ alkoxy groups,
$C_3$-$C_6$ alkenyl optionally substituted with one to three halogen atoms or one phenyl group, or
$C_3$-$C_6$ alkynyl optionally substituted with one to three halogen atoms or one phenyl group; and
$R_1$ is $C_1$-$C_6$ alkyl optionally substituted with one to three halogen atoms,
one hydroxy,
one cyano,
one to two $C_1$-$C_4$ alkoxy groups optionally substituted with one to three halogen atoms,
one $C_1$-$C_4$ alkylthio,
one phenyl optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$ alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkylcarbonyloxy group optionally substituted with one to three halogen atoms,
one $C_2$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$C_6$ alkoxycarbonyl group optionally substituted with one to three halogen atoms or one to three $C_1$-$C_4$ alkoxy groups, or
one benzyloxycarbonyl group optionally substituted on the phenyl ring with one to three halogen atoms, one to three $C_1$-$C_4$ alkyl groups or one to three $C_1$-$C_4$ alkoxy groups,
$C_3$-$C_6$ alkenyl optionally substituted with one to three halogen atoms or one phenyl group,
$C_3$-$C_6$ alkynyl optionally substituted with one to three halogen atoms or one phenyl group,
phenyl optionally substituted with one to three halogen atoms, one or two $C_1$-$C_4$ alkyl groups, one or two $C_1$-$C_4$ alkoxy groups, $CF_3$, CN, $NO_2$, di($C_1$-$C_4$ alkyl)amino or $C_1$-$C_4$ alkanoylamino,
phenoxy optionally substituted with one to three halogen atoms, one or two $C_1$-$C_4$ alkyl groups, one or two $C_1$-$C_4$ alkoxy groups, $CF_3$, CN, $NO_2$, di($C_1$-$C_4$ alkyl)amino or $C_1$-$C_4$ alkanoylamino,
$C_1$-$C_6$ alkoxy optionally substituted with one to three halogen atoms,
$C_2$-$C_6$ alkenyloxy optionally substituted with one to three halogen atoms,
di($C_1$-$C_4$ alkyl)amino,
N-($C_1$-$C_4$ alkyl)-N-phenylamino or -N-halophenylamino, or
$C_3$-$C_6$ polymethyleneimino.

9. The method according to claim 8, wherein the compound is selected from the group consisting of 2-bromo-5-(p-chlorophenyl)-3,4-bis(trifluoromethyl)pyrrole; 3-bromo-2-(p-chlorophenyl)-4,5-bis-(trifluoromethyl)pyrrole-1-carbonitrile; 3-bromo-2-(p-chlorophenyl)-1-(ethoxymethyl)-4,5-bis(trifluoromethyl)pyrrole; 3-bromo-2-(p-chlorophenyl)-4,5-bis(trifluoromethyl)pyrrole; 3-bromo-5-(p-chlorophenyl)-2,4-bis(trifluoromethyl)pyrrole; 3-(p-chlorophenyl)2,4,5-tris(trifluoromethyl)pyrrole; 3-bromo-2-(3,4-dichlorophenyl)4,5-bis(trifluoromethyl)pyrrole; 3-bromo-2-(3,4-dichlorophenyl)-4,5-bis(trifluoromethyl)pyrrole-1-carbonitrile; 3-bromo-2-(3,4-dichlorophenyl)-1-(ethoxymethyl)-4,5-bis(trifluoromethyl)pyrrole; 3-bromo-4-(p-chlorophenyl)-2,5-bis(trifluoromethyl)pyrrole; 3-bromo-2-(3,4-dichlorophenyl)-1-methyl-4,5-bis(trifluoromethyl)pyrrole; 3-bromo-2-(3,4-dichlorophenyl)-1-(1-isopropoxyethyl)-4,5-bis(trifluoromethyl)pyrrole; 3-bromo-4,5-bis(trifluoromethyl)-2-(α-α-α-trifluoro-p-tolyl)pyrrole; and 3-bromo-1-(ethoxymethyl)-4,5-bis(trifluoromethyl)-2-(α-α-α-trifluoro-p-tolyl)pyrrole.

10. A composition for controlling insects and acarina comprising an agronomically acceptable carrier and an insecticidally or acaricidally effective amount of a bis- or tris(trifluoromethyl)arylpyrrole compound as described in claim 1.

11. A method for protecting growing plants from attack by insects and acarina which comprises applying to the foliage of said plants or to the soil or water in which they are growing an insecticidally or acaricidally effective amount of a bis- or tris(trifluoromethyl)arylpyrrole compound having the structure

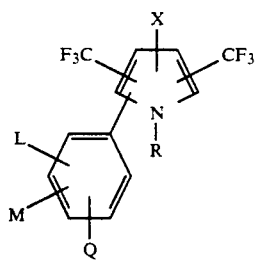

wherein
L is H, F, Cl or Br;
M and Q are each independently H, F, Cl, Br, CN, $NO_2$, $CF_3$, $C_1$-$C_4$ alkyl or $C_1$-$C_3$ alkoxy;
X is Cl, Br, I or $CF_3$;
R is

$$\overset{O}{\underset{}{\|}}CR_1,$$

hydrogen, cyano, $C_1$-$C_6$ alkyl optionally substituted with one to three halogen atoms,
one tri($C_1$-$C_4$ alkyl)silyl,
one hydroxy,
one cyano,
one or two $C_1$-$C_4$ alkoxy groups optionally substituted with one to three halogen atoms,
one $C_1$-$C_4$ alkylthio,
one phenyl optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$ alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkylcarbonyloxy group optionally substituted with one to three halogen atoms,
one $C_1$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$C_6$ alkoxycarbonyl group optionally substituted with one to three halogen atoms or one to three $C_1$-$C_4$ alkoxy groups, or
one benzyloxycarbonyl group optionally substituted on the phenyl ring with one to three halogen atoms, one to three $C_1$-$C_4$ alkyl groups or one to three $C_1$-$C_4$ alkoxy groups,
$C_3$-$C_6$ alkenyl optionally substituted with one to three halogen atoms or one phenyl group, or
$C_3$-$C_6$ alkynyl optionally substituted with one to three halogen atoms or one phenyl group; and
$R_1$ is $C_1$-$C_6$ alkyl optionally substituted with one to three halogen atoms,
one hydroxy,
one cyano,
one or two $C_1$-$C_4$ alkoxy groups optionally substituted with one to three halogen atoms,
one $C_1$-$C_4$ alkylthio,
one phenyl optionally substituted with one to three halogen atoms, one to three $C_1$-$C_4$ alkyl groups or one to three $C_1$-$C_4$ alkoxy groups,
one phenoxy group optionally substituted with one to three halogen atoms, one to three $C_1$-$C_4$ alkyl groups or one to three $C_1$-$C_4$ alkoxy groups,
one benzyloxy group optionally substituted on the phenyl ring with one to three halogen atoms, one to three $C_1$-$C_4$ alkyl groups or one to three $C_1$-$C_4$ alkoxy groups,
one $C_1$-$C_6$ alkylcarbonyloxy group optionally substituted with one to three halogen atoms,
one $C_2$-$C_6$ alkenylcarbonyloxy group optionally substituted with one to three halogen atoms,
one phenylcarbonyloxy group optionally substituted with one to three halogen atoms, one to three $C_1$-$C_4$ alkyl groups or one to three $C_1$-$C_4$ alkoxy groups,
one $C_1$-$C_6$ alkoxycarbonyl group optionally substituted with one to three halogen atoms or one to three $C_1$-$C_4$ alkoxy groups, or
one benzyloxycarbonyl group optionally substituted on the phenyl ring with one to three halogen atoms, one to three $C_1$-$C_4$ alkyl groups or one to three $C_1$-$C_4$ alkoxy groups,
$C_3$-$C_6$ alkenyl optionally substituted with one to three halogen atoms or one phenyl group,
$C_3$-$C_6$ alkynyl optionally substituted with one to three halogen atoms or one phenyl group,
phenyl optionally substituted with one to three halogen atoms, one or two $C_1$-$C_4$ alkyl groups, one or two $C_1$-$C_4$ alkoxy groups, $CF_3$, CN, $NO_2$, di($C_1$-$C_4$ alkyl)amino or $C_1$-$C_4$ alkanoylamino,
phenoxy optionally substituted with one to three halogen atoms, one or two $C_1$-$C_4$ alkyl groups, one or two $C_1$-$C_4$ alkoxy groups, $CF_3$, CN, $NO_2$, di($C_1$-$C_4$ alkyl)amino or $C_1$-$C_4$ alkanoylamino,
$C_1$-$C_6$ alkoxy optionally substituted with one to three halogen atoms,
$C_2$-$C_6$ alkenyloxy optionally substituted with one to three halogen atoms,
di($C_1$-$C_4$ alkyl)amino, N-($C_1$-$C_4$alkyl)-N-phenylamino or -N-halophenylamino, or
$C_3$-$C_6$ polymethyleneimino.

12. The method according to claim 11, wherein the compound is selected from the group consisting of 2-bromo-5-(p-chlorophenyl)-3,4-bis(trifluoromethyl)pyrrole; 3-bromo-2-(p-chlorophenyl)-4,5-bis(trifluoromethyl)pyrrole-1-carbonitrile; 3-bromo-2-(p-chlorophenyl)-1-(ethoxymethyl)-4,5-bis(trifluoromethylpyrrole; 3-bromo-2-(p-chlorophenyl)-4,5-bis(trifluoromethyl)pyrrole; 3-bromo-5-(p-chlorophenyl)-2,4-bis(trifluoromethyl)pyrrole; 3-(p-chlorophenyl)-2,4,5-tris(trifluoromethyl)pyrrole; 3-bromo-2-(3,4-dichlorophenyl)-4,5-bis(trifluoromethyl)pyrrole; 3-bromo-2-(3,4-dichlorophenyl)-4,5-bis(trifluoromethyl)pyrrole-1-carbonitrile; 3-bromo-2-(3,4-dichlorophenyl)-1-(ethoxymethyl)-4,5-bis(trifluoromethyl)pyrrole; 3-bromo-4-(p-chlorophenyl)-2,5-bis(trifluoromethyl)pyrrole; 3-bromo-2-(3,4-dichlorophenyl)-1-methyl-4,5-bis(trifluoromethyl)pyrrole; 3-bromo-2-(3,4-dichlorophenyl)-1-(1-isopropoxyethyl)-4,5-bis(trifluoromethyl)pyrrole; 3-bromo-4,5-bis(trifluoromethyl)-2-(α-α-α-trifluoro-p-tolyl)pyrrole; and 3-bromo-1-(ethoxymethyl)-4,5-bis(trifluoromethyl)-2-(α-α-α-trifluoro-p-tolyl)pyrrole.

13. The method according to claim 11, wherein the compound is applied to the plants or soil in which they are growing at a rate of about 0.1 Kg/ha to 4.0 Kg/ha.

14. The method according to claim 11, wherein the compound is applied to the foliage of the plants or soil or water in which they are growing in the form of a liquid composition containing from about 10 ppm to 10,000 ppm of the compound.

* * * * *